United States Patent [19]

Oxman et al.

[11] Patent Number: 5,256,447
[45] Date of Patent: Oct. 26, 1993

[54] ADHESIVE COMPOSITION AND METHOD

[75] Inventors: Joel D. Oxman, St. Louis Park; Jon W. Fundingsland, Maplewood, both of Minn.

[73] Assignee: Minnesota Mining and Manufacturing Company, St. Paul, Minn.

[21] Appl. No.: 815,171

[22] Filed: Dec. 31, 1991

[51] Int. Cl.$^5$ ............... B05D 5/10; C08F 230/02; C08L 85/02; C08L 33/02
[52] U.S. Cl. ............... 427/207.1; 525/188; 525/221; 526/278; 427/2; 156/327
[58] Field of Search ............... 427/207.1, 208, 208.2, 427/2; 526/278

[56] References Cited

U.S. PATENT DOCUMENTS

| | | | |
|---|---|---|---|
| 3,513,123 | 5/1970 | Saffir | 106/35 |
| 3,574,943 | 4/1971 | Stark et al. | 32/15 |
| 3,882,600 | 5/1975 | Plymale | 32/15 |
| 3,997,504 | 12/1976 | Plymale | 260/42.27 |
| 4,001,483 | 1/1977 | Lee, Jr. et al. | 526/270 |
| 4,064,629 | 12/1977 | Stoner et al. | 32/15 |
| 4,222,780 | 9/1980 | Shibatani et al. | 106/35 |
| 4,235,633 | 11/1980 | Tomioka et al. | 106/35 |
| 4,259,075 | 3/1981 | Yamauchi et al. | 433/217 |
| 4,259,117 | 3/1981 | Yamauchi et al. | 106/35 |
| 4,368,043 | 1/1983 | Yamauchi et al. | 433/217 |
| 4,383,052 | 5/1983 | Higo et al. | 523/118 |
| 4,499,251 | 2/1985 | Omura et al. | 526/278 |
| 4,514,342 | 4/1985 | Billington et al. | 260/952 |
| 4,515,930 | 5/1985 | Omura et al. | 526/276 |
| 4,537,940 | 8/1985 | Omura et al. | 526/276 |
| 4,539,382 | 9/1985 | Omura et al. | 526/276 |
| 4,544,467 | 10/1985 | Bunker et al. | 204/159.24 |

FOREIGN PATENT DOCUMENTS

| | | |
|---|---|---|
| 0058483 | 8/1982 | European Pat. Off. |
| 2561521 | 9/1985 | France |
| 57-143372 | 9/1982 | Japan |
| 57-167364 | 10/1982 | Japan |
| 63-175085 | 7/1988 | Japan |
| 63-250310 | 10/1988 | Japan |

OTHER PUBLICATIONS

M. Buonocore, W. Wileman, and F. Brudevold, *J. Dent. Res.*, 35, 846 (1956).
M. Buonocore and M. Quigley, *J. Amer. Dent. Assoc.*, 57, 807 (1958).
M. Anbar and E. Farley, *J. Dent. Res.*, 53, 879 (1974).
E. Farley, R. Jones, and M. Anbar, *J. Dent. Res.*, 56, 943 (1977).
M. Staninec and M. Holt, *Journal of Prosthetic Dentistry* (1988), vol. 59, pp. 397-402.
A. Lacey and M. Staninec, *Quintessence International* (1989), vol. 20, pp. 521-524.
Y. Aboush and C. Jenkins, *Br. Dent. J.* (1989), vol. 166, pp. 255-257.
Y. Aboush and R. Elderton, *Br. Dent. J.* (1991), vol. 170, pp. 219-222.
Y. Aboush and R. Elderson, *Dent. Mater.* (1991), vol. 7, pp. 130-132.
A. Ben-Amar, *J. Am. Dent. Assoc.* (1989), vol. 119, pp. 725-728.
M. Mitrosky, Jr., *Quintessence International* (1981), vol. 9, pp. 871-874.
H. J. Staehle et al., *Dtsch. Zahnartzt* (1988), vol. 43, pp. 952-957.

*Primary Examiner*—Joseph L. Schofer
*Assistant Examiner*—Wu C. Cheng
*Attorney, Agent, or Firm*—Gary L. Griswold; Walter N. Kirn; Dale A. Bjorkman

[57] ABSTRACT

An adhesive composition comprising an ethylenically unsaturated phosphorylated compound, a carboxylic acid functional polymer, and a polymerization initiator, and optionally comprising a particulate metallic filler. Also disclosed is a method of adhering a restorative material such as amalgam to hard tissue such as dentin or enamel, involving the use of an adhesive composition of the invention as an intermediate layer between the restorative material and the hard tissue.

12 Claims, No Drawings

ADHESIVE COMPOSITION AND METHOD

BACKGROUND OF THE INVENTION

1. Technical Field

This invention relates to adhesive compositions comprising a phosphorylated compound. In another aspect, this invention relates to adhesive compositions comprising a carboxylic acid functional polymer. This invention also relates to methods of adhering a restorative material to a substrate, and in another aspect to methods of adhering a dental restorative such as amalgam to hard tissue such as dentin or enamel.

2. Description of the Related Art

Dental amalgams and restorative composites are used extensively for intracoronal and extracoronal restorations. Amalgam, however, does not adhere to tooth structure and the dentist must prepare the tooth cavity with dovetails and various cutout grooves that mechanically lock the amalgam into the cavity. Such preparation, however, results in excavation of more tooth structure than would otherwise be necessary if there was good adhesion between the tooth structure and the amalgam. Moreover, leakage at the interface of the amalgam and cavity wall (known as "microleakage") tends to occur. This microleakage allows penetration of bacteria, soluble salts, and saliva into any space between the amalgam and tooth structure. This can lead to inflammation, pulp irritation, demineralization of the tooth, corrosion of the amalgam, and other attendant complications. An adhesive seal between amalgam and tooth structure could minimize and/or prevent microleakage and allow for a stronger restoration due to excavation of less tooth material.

Products claiming to make amalgam adhesive to tooth structure are available. One such product is sold in a kit under the trademark AMALGAMBOND TM (Parkell Co.). This product is a liquid adhesive to be coated directly onto tooth structure. The active ingredients in the adhesive include 4-META (4-methacryloxyethyl trimellitic anhydride) and TBB (tri-n butyl borane). Other products which similarly involve coating a specific curable resin directly onto tooth structure to make amalgam adhere are available under the trademarks PANAVIA TM Dental Adhesive (Kuraray Company) and SUPERBOND TM Adhesive (Sun Medical Co., Ltd., Kyoto, Japan). These latter products also are difficult to employ, since there are a number of required preparatory steps for their application and curing.

Adhesive compositions that employ phosphoruscontaining free-radically polymerizable compounds have been reported in the literature, see, e.g., M. Buonocore, W. Wileman, and F. Brudevold, *J. Dent. Res.*, 35, 846 (1956), M. Buonocore and M. Quigley, *J. Amer. Dent. Assoc.*, 57, 807 (1958), M. Anbar and E. Farley, *J. Dent. Res.*, 53, 879 (1974), E. Farley, R. Jones, and M. Anbar, *J. Dent. Res.*, 56 1943 (1977), U.S. Pat Nos. 3,882,600, 3,997,504, 4,222,780, 4,235,633, 4,259,075, 4,259,117, 4,368,043, 4,383,052, 4,499,251, 4,514,342, 4,515,930, 4,537,940, 4,539,382, and 4,544,467, European published patent application No. 0 058 483, and Japanese laid-open patent application (Kokai) Nos. 57-143372 and 57-167364.

U.S. Pat. No. 3,513,123 (Saffir) describes a curable epoxy composition that can be added to amalgam in order to make the amalgam adhere to tooth structure. The curable epoxy composition contains a glycidyl ether type resin and a polyamine hardening agent.

U.S. Pat. No. 4,064,629 (Stoner) describes a method for applying amalgam restorations. The method involves precoating the surfaces of a cavity within a carious tooth with a layer of an "adhesive-metal" lining composition. The metal of the lining composition is amalgamated by diffusion of the mercury from the subsequently applied conventional dental amalgam filling. The "adhesive-metal" lining composition is said to improve corrosion resistance of the dental amalgam filling and also to promote bonding between the amalgam restoration and the cavity surfaces.

U.S. Pat. No. 4,001,483 (Lee, Jr. et al.) describes dental compositions for sealing margins between tooth structures and amalgam restorations therein, the compositions containing (a) an alkylene glycol dimethacrylate and/or its oligomer, (b) a polymerization initiator, (c) a polymerization accelerator and (d) a secondary monomer additive.

U.S. Pat. No. 3,574,943 (Stark) describes a method of restoring a carious tooth whereby the cavity is excavated, lined with a layer of a polysiloxane pressure sensitive adhesive polymer dissolved in a fluorocarbon, and filled with amalgam. The polysiloxane layer is said to act as a barrier to leakage.

Further articles that describe bonding of amalgam to tooth structure by precoating the tooth with adhesive resin include M. Staninec and M. Holt, *Journal of Prosthetic Dentistry* (1988), Vol. 59, pp. 397–402, A. Lacey and M. Staninec, *Quintessence International* (1989), Vol. 20, pp. 521–524, Y. Aboush and C. Jenkins, *Br. Dent. J.* (1989), Vol. 166, pp. 255–257, Y. Aboush and R. Elderton, *Br. Dent. J.* (1991), Vol. 170, pp. 219–222, and Y. Aboush and R. Elderton, *Dent. Mater.* (1991), Vol. 7, pp. 130–132. The last article involves adhesion to previously hardened amalgam, whereas the other articles involve adhesion to fresh amalgam. Also, A. Ben-Amar, *J. Am. Dent. Assoc.* (1989) Vol. 119, pp. 725–728, describes a reduction in microleakage at the margins of amalgam restorations when "SCOTCHBOND" Dual Cure Dental Adhesive resin (3M) is applied to cavity margins prior to application of amalgam, and M. Mitrosky, Jr., *Quintessence International* (1981) Vol. 9, pp. 871–874, describes the use of ethyl cyanoacrylate as a bonding agent beneath amalgam and composite restoratives. H. J. Staehle et al., *Dtsch. Zahnartzt* (1988) Vol. 43, pp. 952–957, describes the use of various dental adhesives and varnishes to adhere amalgam to dentin.

Japanese Kokai 63-175085 describes an adhesive composition comprising an acid functional monomer, polymer, or copolymer, a vinyl monomer in which the acid functional component is soluble, an organic peroxide, and an aromatic amine or sulfinate salt. The composition is said to bond living tooth tissue to composites and amalgams.

French Patent 2,561,521 describes an intermediate adhesive composition for sealing dental cavities and chemically securing amalgams, comprising a metal powder dispersed in an adhesive varnish. The composition contains metal powder, cellulosic varnish, ethyl acetate, amyl propionate, fluoride, and oil of pimento leaf.

Japanese Kokai 63-250310 describes dental adhesive compositions containing (a) cellulose ether, (b) a vinyl monomer, (c) an organic peroxide, and (d) an aromatic amine or a sulfinate. The composition is said to be applicable to a wide variety of restorative materials, including composite resins, amalgam, alumina, gold, alloys, polymethyl methacrylate, polycarbonate, and the like.

SUMMARY OF THE INVENTION

This invention provides an adhesive composition, comprising:

(i) an ethylenically unsaturated phosphorylated compound;

(ii) a carboxylic acid functional polymer in an amount effective to increase adhesion of amalgam to tooth structure when the composition is used as an intermediate layer between the amalgam and the tooth structure, compared to the adhesion obtained using a like composition absent the carboxylic acid functional polymer; and (iii) a polymerization initiator in an amount sufficient to effect cure of the composition. Such a composition of the invention optionally further comprises a particulate metallic filler in an amount effective to increase adhesion of amalgam to tooth structure when the composition is used as an intermediate layer between the amalgam and the tooth structure, compared to the adhesion obtained using a like composition absent the particulate metallic filler.

This invention also provides an adhesive composition, comprising:

(i) an ethylenically unsaturated phosphorylated compound (ii) a carboxylic acid functional polymer in an amount of about 5 to about 200 parts by weight based on 100 parts by weight of the phosphorylated compound; and (iii) a polymerization initiator in an amount sufficient to effect cure of the composition. These compositions optionally contain a particulate metallic filler in an amount of about 50 to about 4000 parts by weight based on 100 parts by weight of the phosphorylated compound and the carboxylic acid functional polymer.

This invention also provides a method of adhering a restorative material to a substrate, comprising the steps of:

(i) combining the components of a composition of the invention as described above;

(ii) placing an intermediate layer of the composition from step (i) on one member of the restorative material/substrate pair;

(iii) optionally curing the intermediate layer; and (iv) adhering the other member of the restorative material/substrate pair to the first member by way of the intermediate layer.

DETAILED DESCRIPTION OF THE INVENTION

Materials suitable for use as the ethylenically unsaturated phosphorylated compound in a composition of the invention include such materials known to those skilled in the art to be capable of bonding to hard tissue such as dentin, enamel, bone, or the like. This compound, sometimes referred to herein as the "phosphorus compound", is a monomer, oligomer, or polymer (or mixture thereof), preferably suitable for use in the oral environment both in its unpolymerized and polymerized state.

Suitable phosphorus compounds comprise one or more phosphorus atoms bonded through a carbon, nitrogen, oxygen, or sulfur atom, to a radical containing one or more ethylenically unsaturated groups. Preferred ethylenically unsaturated groups are ethenyl and 2-propenyl as found, respectively, in acrylate and methacrylate groups. One or more of the phosphorus atoms can be bonded to one or more halogen atoms, active hydrogen atoms, or substituted or unsubstituted hydrocarbyl groups (e.g., an alkyl, aryl, alkaryl, or aryalkyl group). A particular class of suitable phosphorus compounds is described in European Patent Application No. 0 058 483 and U.S. Pat. No. 4,515,930, the disclosures of which are incorporated herein by reference. These phosphorus compounds include those comprising an organic ester of one or more acids of phosphorus, the organic radical of said ester containing at least one ethylenically unsaturated group, wherein said ester has chlorine or bromine bonded directly to the phosphorus (hereinafter referred to as "halophosphorus acid esters"). A preferred subclass of such halophosphorus acid esters includes halophosphorus acid esters of diglycidyl methacrylate of Bisphenol A ("Bis-GMA") prepared by reacting Bis-GMA with a phosphorus acid. Phosphorus acid halides (e.g., chlorides, bromides) that can be reacted with Bis-GMA include $POCl_3$, $PCl_3$, $PBr_3$, $R'OP(O)Cl_2$, $(R'O)_2P(O)Cl$ where $R'$ is a hydrocarbyl radical, preferably one derived from removal of one or more hydroxyl groups from a hydroxyl-containing compound such as 2-hydroxyethyl methacrylate, ethylene glycol, polyethylene glycol, pentaerythritol, and the like, as would result from a reaction of the hydroxyl-containing compound and the phosphorus acid halide. A particularly preferred class of phosphorus compounds includes chlorophosphorus acid esters of Bis-GMA.

An additional suitable class of phosphorus compounds includes the phosphorus acid esters described in U.S. Pat. Nos. 3,882,600, 3,997,504, 4,222,780, 4,235,633, 4,259,075, 4,259,117, 4,368,043, 4,442,239, 4,499,251, 4,514,342, 4,537,940, 4,539,382 and Japanese published patent application (Koho) No. 85-17235, the disclosures of which are incorporated herein by reference. Exemplary members of this class are the compounds 2-methacryloyloxyethyl phenyl phosphate and 10-methacryloyloxydecyl dihydrogen phosphate.

A further suitable class of phosphorus compounds includes the pyrophosphate ester derivatives described in U.S. Pat. Nos. 4,383,052 and 4,404,150 and in Japanese Kokai 57-143372 and 57-167364, the disclosures of which are incorporated herein by reference.

A further suitable phosphorus compound is glycerophosphate dimethacrylate, described in the above-mentioned Buonocore, Wileman, and Brudevold publication, the disclosure of which is incorporated by reference.

Either a single phosphorus compound or a mixture of phosphorus compounds can be used. The phosphorus compound can be prepared using methods known to those skilled in the art. It can also be obtained from existing commercially available dental adhesives, such as "SCOTCHBOND TM" Dual Cure Dental Adhesive (3M), "ALL-BOND2 TM" Universal Dental Adhesive System (Bisco, Inc.), "CLEARFIL TM" Photo Bond Light-Cured Dental Bonding Agent (Kuraray Co., Ltd.), "RESTOBOND 3 TM" Dual Dentin/Enamel Bonding Agent (Lee Pharmaceuticals, see U.S. Pat. Nos. 4,524,527 and 4,521,550), "PRISMA UNIVERSAL BOND3 TM" Dentin/Enamel Bonding Agent (L. D. Caulk Division of Dentsply International, Inc., see U.S. Pat. No. 4,814,423), "BONDLITE TM" Dental Adhesive (Sybron Corp.), "Johnson & Johnson" Dentin Bonding Agent and "Johnson & Johnson" Light-Curing Bonding Agent (Johnson & Johnson Co.), "PAL- FIQUE ™" Bonding Agent (Tokuyama Soda Co., Ltd.), "SHOFU ™" Bonding Base (Shofu, Inc.), and "SINTERBOND ™" Dental Adhesive (Teledyne Getz).

The carboxylic acid functional polymer is preferably suitable for use in the mouth. Materials suitable for use as the carboxylic acid functional polymer include those homopolymers and copolymers of unsaturated mono-, di-, or tricarboxylic acids known to those skilled in the art to be commonly used in glass ionomer cements. Representative materials are described, for example, in U.S. Pat. Nos. 3,655,605, 4,016,124, 4,089,830, 4,143,018, 4,342,677, 4,360,605, and 4,376,835, and European Published Patent Application No. 88-312127, the disclosures of which are incorporated herein by reference.

Also suitable are those carboxylic acid functional polymers prepared by the homopolymerization and copolymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate. Ter- and higher polymers can also be used.

The carboxylic acid functional polymer can also contain ethylenically unsaturated groups such as ethenyl and 2-propenyl. Such materials can be prepared by reacting a carboxylic acid functional polymer with an ethylenically unsaturated compound comprising at least one group capable of reacting with the carboxylic acid groups of the polymer. Suitable functional groups include —OH, —NCO, —COCl, and

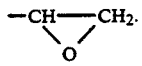

Exemplary compounds include acryloyl chloride, methacryloyl chloride, allyl isocyanate, 2-hydroxyethyl methacrylate, and 2-isocyanatoethyl methacrylate. A particularly preferred carboxylic acid functional polymer is a methacrylate-functional copolymer of itaconic acid and acrylic acid as disclosed in Example 11 of European Published Pat. Application No. 0 323 120.

In particular embodiments, the carboxylic acid functional polymer is present in an amount effective to increase the adhesion of amalgam to tooth structure when the composition is used as an intermediate layer between the amalgam and the tooth structure, compared to the adhesion obtained using a like composition absent the carboxylic acid functional polymer. An effective amount of carboxylic acid functional polymer in these embodiments can be determined according to the method set forth in the EXAMPLES that follow.

In other embodiments, the carboxylic acid functional polymer is present in an amount of about 5 to about 200 parts by weight, preferably about 20 to about 200 parts by weight, based on 100 parts by weight of the phosphorylated compound.

A composition of the invention also includes a polymerization initiator in an amount sufficient to effect cure of the composition. Suitable polymerization initiators include autocure and light cure initiators such as those mentioned in columns 28 and 29 of U.S. Pat. No. 4,539,382, chromophore-substituted halomethyl-s-triazines such as those shown in U.S. Pat. No. 3,954,475, and chromophore-substituted halomethyloxadiazoles such as those shown in U.S. Pat. No. 4,212,970.

The polymerization initiator is preferably present in an amount of about 0.01 to about 20 parts by weight, more preferably about 0.1 to about 10 parts by weight based on 100 parts by weight of the phosphorylated compound and the carboxylic acid functional polymer.

The compositions of the invention preferably further comprise a particulate metallic filler. The filler can be a pure metal such as those of Groups IVA, VA, VIA, VIIA, VIII, IB, and IIB, aluminum, indium, or thallium of Group IIIB, or tin or lead of Group IVB, or alloys thereof. Conventional dental amalgam alloy powders, typically mixtures of silver, tin, copper, and zinc, are also suitable. The particulate metallic filler preferably has an average particle size of about 1 micron to about 100 microns, more preferably 1 micron to about 50 microns.

In some embodiments, the optional metallic filler is present in an amount effective to increase adhesion of amalgam to tooth structure when the composition is used as an intermediate layer between the tooth structure and the amalgam, compared to the adhesion obtained using a like composition absent the metallic filler. An effective amount in these embodiments can be determined according to the method set forth in the EXAMPLES that follow. In other embodiments the particulate metallic filler is present in an amount of 50 to about 4000 parts by weight, preferably about 200 to about 3000 parts by weight based on 100 parts by weight of the phosphorylated compound and the carboxylic acid functional polymer.

Ethylenically unsaturated compounds (other than the phosphorylated compound) can be incorporated in the compositions of the invention in appropriate amounts easily selected by those skilled in the art. Suitable compounds include mono- or poly- acrylates and methacrylates such as methyl acrylate, 2-hydroxyethyl acrylate, triethyleneglycol diacrylate, neopentylglycol diacrylate, hexamethyleneglycol diacrylate, trimethylolpropane triacrylate, pentaerythritol tetraacrylate, polyalkylene glycol mono- and di-acrylates, urethane mono- or poly-functional acrylates, Bisphenol A diacrylates, and the corresponding methacrylates of the above compounds, as well as acrylamides and methacrylamides, vinyl compounds, styrene compounds, and other olefinically unsaturated compounds suitable for use in the oral environment. U.S. Pat. Nos. 4,499,251, 4,515,930, 4,537,940 and 4,539,382 contain lists of such compounds.

The compositions can also contain conventional adjuvants such as solvents, accelerators, inhibitors, stabilizers, pigments, dyes, viscosity modifiers, extending or reinforcing fillers, surface tension depressants, wetting aids, antioxidants, and other ingredients known to those skilled in the art.

The compositions can be mixed like conventional dental materials according to methods well known to those skilled in the art. Ordinarily it is preferred to add the carboxylic acid functional polymer to the phosphorylated compound, followed by the addition of the polymerization initiator. Some carboxylic acid functional polymers may be difficult to dissolve in or mix with the phosphorylated compound. In such cases a volatile, removable cosolvent such as ethanol, methylene chloride, acetone, ethyl acetate, methyl ethyl ketone or tetrahydrofuran ("THF") can aid mixing. The cosolvent can then be removed from the dental material such as by vacuum and optional heating.

The compositions of the invention can be packaged according to methods well known to those skilled in the art. For example, when a redox type polymerization initiator is used, an appropriate package form keeps the oxidant and the reducing agent apart from each other in order to ensure storage stability of the composition. Examples of package forms include: (i) two-part packages of (a) a phosphorylated compound, a carboxylic acid functional polymer, and a reducing agent in one part and (b) a phosphorylated compound and an oxidant in the other; (ii) two-part packages of (a) a phosphorylated compound and one element of a redox pair, and (b) a carboxylic acid functional polymer and the other element of the redox pair; and (iii) two-part packages of (a) a phosphorylated compound and an oxidant and (b) a phosphorylated compound, a carboxylic acid functional polymer, and a reducing agent. In the case of an organic sulfinic acid (or salt thereof)/amine (or salt thereof)/peroxide ternary system, it is also possible to use a three-part package form in which the sulfinic acid and the amine are packaged separately. The optional particulate metallic filler component can be included in any or all parts of the above-described package forms.

Where the polymerization initiator comprises a photoinitiator, the phosphorylated compound and the photoinitiator are preferably packaged separately or in a container opaque to light. With a thermal curing agent that initiates polymerization when it is brought into contact with the phosphorylated compound (e.g., tributyl borane), the phosphorylated compound and the curing agent are packaged separately. Such separately packaged components are mixed together shortly before use.

A composition of the invention can be used as an intermediate layer between a substrate such as hard tissue (e.g., bone, enamel, or dentin), ceramic, porcelain, and the like, and a restorative material such as a pure metal or alloy, an amalgam, a ceramic composite, or a composite comprising an adhesive polymer (or a mixture of polymers) and a particulate inorganic filler. A primer can be used, but good adhesion is obtained without the use of auxiliary primers, and the compositions of the invention generally provide better adhesion than is obtained using the phosphorylated compound alone.

In order to adhere a restorative material to a substrate, the components of a composition of the invention are first combined in appropriate amounts. As discussed above, depending upon the particular type of polymerization initiator used the components can be mixed prior to packaging or they can be packaged as two- or three-part systems and combined just prior to use. Once the components are combined the resulting composition of the invention can be placed in the form of a thin layer (e.g., by brushing) on either the substrate or on the restorative material. The layer can then optionally be cured by appropriate means (e.g., heat including exposure to room temperature, visible light, ultraviolet light, or the like). The other of the restorative material/substrate pair can then be prepared (e.g., mixed) if necessary and placed on the adhesive layer.

For the reasons set forth above in connection with the Background of the Invention, it is desirable if an amalgam can be made to adhere well to tooth structure. Accordingly, one use of the compositions of the invention involves adhering dental amalgam to tooth structure in a prepared cavity.

It is preferred to use a modified amalgam in order to optimize adhesion to tooth structure. Modified amalgams are disclosed in commonly assigned copending application 07/638,614, incorporated herein by reference. Such a modified amalgam can be produced by admixing particulate additives into conventional amalgam alloy powder. The modified amalgam is then prepared in a conventional manner by triturating the modified alloy powder with mercury in an amalgamator.

The preferred particulate additives are selected from the following groups: 1) acrylate- or methacrylate-functional polymers, 2) metal salts of acrylates or methacrylates, 3) nonmetallic fillers, 4) oxidizing agents, and 5) reducing agents. The particulate additives are applicable to the full range of conventional amalgam alloy powders and conventional weight ratios of mercury to amalgam alloy powder.

Representative acrylate- or methacrylate-functional polymers include poly(alkanoic acid) powder. Representative metal salts of acrylates or methacrylates include zinc dimethacrylate, zirconium dimethacrylate, silver methacrylate, sodium methacrylate, and magnesium methacrylate. Nonmetallic fillers include both untreated organic fillers and surface-treated fillers. Representative nonmetallic fillers, also known as organic fillers, include blends of silane-treated OX-50 TM pyrogenic silica (Degussa Company), tetraethyleneglycol dimethacrylate ("TEGDMA") (Rohm Tech Co.), and Bisphenol A diglycidylether dimethacrylate in a 60:17:17 weight ratio. Other representative nonmetallic fillers include zirconia/silica filler either untreated or pretreated with gamma-methacryloxypropyl trimethoxysilane as described in U.S. Pat. No. 4,503,169. Preferred oxidizing agents include benzoyl peroxide. Preferred reducing agents include sodium benzenesulfinate.

Adhesion of amalgam to etched enamel was evaluated as follows: Bovine teeth of similar age and appearance were partially embedded in circular acrylic disks such that the enamel was exposed. The exposed portion of each tooth was ground flat and parallel to the acrylic disc using Grade 120 silicon carbide paper-backed abrasive mounted on a lapidary wheel. Further grinding and polishing of the teeth was carried out by mounting Grade 320 silicon carbide paper-backed abrasive on the lapidary wheel. During the grinding and polishing steps, the teeth were continuously rinsed with water. The polished teeth were stored in distilled water and used for testing within 2 hours after polishing.

The polished teeth were removed from the water and dried using a stream of compressed air. Phosphoric acid etching gel was applied to the enamel for 15 seconds, rinsed with water, and dried. The adhesive composition was applied to the entire enamel surface with a brush and blown into a thin film with compressed air and cured for 10 seconds with a VISILUX TM 2 dental curing light (3M).

A mold made from a 2 mm thick TEFLON TM polytetrafluoroethylene sheet with a 5 mm diameter circular hole through the sheet was clamped to each polished tooth so that the central axis of the hole in the mold was normal to the polished tooth surface. The hole in each mold was filled with a prepared amalgam and allowed to stand for about 15 minutes at room temperature, then stored in distilled water at 37° C. for 24 hours. The molds were then carefully removed, leaving a molded button of amalgam attached to each tooth.

Adhesive strength was evaluated by mounting the acrylic disk in a holder clamped in the jaws of an INSTRON ™ testing apparatus with the polished tooth surface oriented parallel to the direction of pull. A loop of orthodontic wire (0.44 mm diameter) was placed around the base of the amalgam button adjacent to the polished tooth surface. The ends of the orthodontic wire were clamped in the pulling jaw of the tensile testing apparatus, placing the bond in shear stress. The bond was stressed until it (or the amalgam button) failed, using a crosshead speed of 2 mm/min.

The following are offered to aid in understanding of the present invention and are not to be construed as limiting the scope thereof. Unless otherwise indicated, all parts and percentages are by weight.

EXAMPLES 1–7 and COMPARATIVE EXAMPLES C-1 through C-5

Using the procedure set forth above, the adhesive shear bond strength on etched enamel of several adhesive compositions was evaluated. The amalgam used was a two-spill capsule of DISPERSALLOY ™ amalgam. Various amounts of an ethylenically unsaturated phosphorylated compound (SCOTCHBOND ™ Dual Cure Dental Adhesive resin), a sodium benzene sulfinate polymerization initiator (SCOTCHBOND ™ Dual Cure Dental Adhesive liquid), a carboxylic acid functional polymer (VITREBOND ™ polymer), and a particulate metallic filler (TYTIN ™ alloy powder) were combined, mixed, and applied to the etched enamel. Set out below in TABLE I are the example numbers, amounts of components and mean adhesive shear bond values for the samples tested.

use of a particulate metallic filler further increases adhesion.

We claim:

1. A method of adhering a restorative material to a substrate, comprising the steps of:
   (i) combining the components of an adhesive composition comprising:
       (a) an ethylenically unsaturated phosphorylated compound;
       (b) a carboxylic acid functional polymer in an amount effective to increase adhesion of amalgam to tooth structure when the composition is used as an intermediate layer between the amalgam and the tooth structure, compared to the adhesion obtained using a like composition absent the carboxylic acid functional polymer; and
       (c) a curing agent in an amount sufficient to effect cure of the composition;
   (ii) placing an intermediate layer of the composition from step (i) on one member of the restorative material/substrate pair;
   (iii) optionally curing the intermediate layer; and
   (iv) adhering the other member of the restorative material/substrate pair to the first member by way of the intermediate layer.

2. A method of adhering a restorative material to a substrate, comprising the steps of:
   (i) combining the components of an adhesive composition comprising:
       (a) an ethylenically unsaturated phosphorylated compound;
       (b) a carboxylic acid functional polymer in an amount of about 5 to about 200 parts by weight based on 100 parts by weight of the phosphorylated compound; and

TABLE I

ADHESION OF AMALGAM TO ETCHED ENAMEL

| Ex. No. | Phosphorylated Compound[1] (g) | Polymerization Initiator[2] (g) | Carboxylic Acid Functional Polymer[3] (g) | Method of Addition of Carboxylic Acid Functional Polymer | Metal Filler[4] (g) | Number of Samples | Mean Shear Adhesion (kg/cm$^2$) | Std. Dev. |
|---|---|---|---|---|---|---|---|---|
| C-1 | 0.03 | 0.012 | — | — | — | 55 | 10.7 | 15.7 |
| C-2 | — | — | 0.032 | In ethanol | — | 5 | 0.0 | 0.0 |
| C-3 | — | 0.012 | 0.032 | In ethanol | — | 5 | 0.0 | 0.0 |
| 1 | 0.03 | 0.012 | 0.005 | In phosphorylated compound | — | 10 | 42.3 | 10.8 |
| 2 | 0.03 | 0.012 | 0.010 | In phosphorylated compound | — | 20 | 38.7 | 29.7 |
| 3 | 0.03 | 0.012 | 0.015 | In phosphorylated compound | — | 15 | 42.3 | 13.9 |
| 4 | 0.03 | 0.012 | 0.020 | In phosphorylated compound | — | 18 | 30.5 | 25.5 |
| 5 | 0.03 | 0.012 | 0.003 | In ethanol | — | 5 | 22.8 | 16.5 |
| 6 | 0.03 | 0.012 | 0.006 | In ethanol | — | 5 | 50.0 | 14.0 |
| C-4 | 0.03 | 0.012 | — | — | 0.40 | 5 | 75.5 | 22.7 |
| C-5 | — | 0.024 | 0.006 | In ethanol | 0.40 | 5 | 0.0 | 0.0 |
| 7 | 0.03 | 0.012 | 0.006 | In ethanol | 0.40 | 5 | 85.7 | 11.5 |

[1]SCOTCHBOND ™ Dual Cure dental Adhesive resin.
[2]SCOTCHBOND ™ Dual Cure Dental Adhesive liquid.
[3]Poly(alkanoic acid) powder prepared according to Example 11 of European Published Pat. Application No. 0 323 120.
[4]TYTIN ™ Alloy.

The results in TABLE I show that a composition containing an ethylenically unsaturated phosphorylated compound, a carboxylic acid functional polymer, and a curing agent results in a synergistic enhancement of adhesive shear bond strength of etched enamel to amalgam relative to any other two component combination of the three components. The results also show that the (c) a polymerization initiator in an amount sufficient to effect cure of the composition;
   (ii) placing an intermediate layer of the composition from step (i) on one member of the restorative material/substrate pair;
   (iii) optionally curing the intermediate layer; and (iv) adhering the other member of the restorative material/substrate pair to the first member by way of the intermediate layer.

3. A method according to claim 1, wherein the ethylenically unsaturated phosphorylated compound comprises a chlorophosphorus acid ester of diglycidyl methacrylate of Bisphenol A.

4. A method according to claim 1, wherein the carboxylic acid functional polymer is a methacrylate functional copolymer of itaconic acid and acrylic acid.

5. A method according to claim 1, further comprising a particulate metallic filler in an amount effective to increase adhesion of amalgam to tooth structure when the composition is used as an intermediate layer between the amalgam and the tooth structure, compared to the adhesion obtained using a like composition absent the particulate metallic filler.

6. A method according to claim 5, wherein the ethylenically unsaturated phosphorylated compound comprises a chlorophosphorus acid ester of diglycidyl methacrylate of Bisphenol A.

7. A method according to claim 5, wherein the carboxylic acid functional polymer is a methacrylate-functional copolymer of itaconic acid and acrylic acid.

8. A method according to claim 2, wherein the ethylenically unsaturated phosphorylated compound comprises a chlorophosphorus ester of diglycidyl methacrylate of Bisphenol A.

9. A method according to claim 2, wherein the carboxylic acid functional polymer is a methacrylate-functional copolymer of itaconic acid and acrylic acid.

10. A method according to claim 2, further comprising a particulate metallic filler in an amount of about 50 to about 4000 parts by weight based on 100 parts by weight of the phosphorylated compound and the carboxylic acid functional polymer.

11. A method according to claim 10, wherein the ethylenically unsaturated phosphorylated compound comprises a chlorophosphorus acid ester of diglycidyl methacrylate of Bisphenol A.

12. A method according to claim 10, wherein the carboxylic acid functional polymer is a methacrylate-functional copolymer of itaconic acid and acrylic acid.

* * * * *